United States Patent [19]

Young et al.

[11] 4,283,387
[45] Aug. 11, 1981

[54] ADHERENT CONTROLLED RELEASE PESTICIDE

[75] Inventors: Robert W. Young, New York, N.Y.; Samuel Prussin, Big Sur, Calif.; Norman G. Gaylord, New Providence, N.J.

[73] Assignee: Young, Prussin, MGK, J.V., New York, N.Y.

[21] Appl. No.: 92,632

[22] Filed: Nov. 8, 1979

[51] Int. Cl.³ ............................................. A01N 25/24
[52] U.S. Cl. ...................................... 424/78; 71/64 F; 424/77; 424/81; 424/82; 427/4
[58] Field of Search ...................... 424/77, 78, 81, 82; 71/64 F

[56] References Cited

U.S. PATENT DOCUMENTS

| 4,172,904 | 10/1979 | Young et al. | 424/78 X |
| 4,190,680 | 2/1980 | Young et al. | 424/78 X |

Primary Examiner—Richard Raymond
Attorney, Agent, or Firm—Roylance, Abrams, Berdo & Farley

[57] ABSTRACT

There are disclosed methods and compositions for the controlled release of pesticides by using a mixture comprising: (a) a carbinol-containing organic polymer; crosslinking agents for said polymer consisting essentially of (b) a hydrolyzable silane or an organopolysiloxane containing hydrolyzable silane groups or partial hydrolyzates thereof and (c) a hydrolyzable organic titanium compound or a partial hydrolyzate thereof; and (d) a pesticide.

10 Claims, No Drawings

ADHERENT CONTROLLED RELEASE PESTICIDE

FIELD OF THE INVENTION

This invention relates to methods and compositions for the controlled release of bioactive agents and, more particularly, to the controlled release of pesticides. The present invention is concerned with stable compositions which after application to a suitable substrate and exposure to the atmosphere, undergo in situ chemical reaction resulting in adherent bioactive agents with controlled release characteristics.

BACKGROUND OF THE INVENTION

The utilization of bioactive agents such as pesticides, e.g., insecticides, herbicides and fungicides has become an important fact of life. However, these materials are generally effective only as long as they persist on the substrate to which they are applied.

The basic motivation underlying the modern development of controlled release pesticidal materials has been to extend the duration between applications and thus increase the efficiency and hence economy of control. Controlled release of pesticides permits extended time intervals between treatments and reduction of the dosage, thus reducing environmental impact. Thus, from an ecological standpoint, controlled release of pesticides enhances the lifetime of a non-persistent agent at the site of treatment while maintaining the preferred property of rapid detoxification in the environment surrounding the controlled release pesticide.

The desired controlled release of pesticides has previously been achieved by their incorporation within a polymeric matrix, e.g., encapsulation wherein a pest control agent is surrounded by an enveloping polymeric wall that permits loss through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment. However, the prior art approaches fall short of the desired goal in that there is not adequate provision for the adhesion of the pesticide within the polymeric matrix to the substrate. This permits the removal or transfer of the material from the substrate as a result of physical contact, wind, rain or other atmospheric conditions.

SUMMARY OF THE INVENTION

An object of the present invention is to provide a process for the controlled release of bioactive agents such as pesticides, removing the above-described defects of the prior art processes. Another object of the present invention is to provide compositions capable of undergoing in situ chemical reaction after application to a substrate and exposure to the atmosphere, resulting in adhesion of the bioactive agent and increased effective lifetime.

It has now been found that these improvements in controlled release pesticides are achieved by using a mixture comprising: (a) a carbinol-containing organic polymer; crosslinking agents for said polymer consisting essentially of (b) a hydrolyzable silane or an organopolysiloxane containing hydrolyzable silane groups or partial hydrolyzates thereof and (c) a hydrolyzable organic titanium compound or a partial hydrolyzate thereof; and (d) a pesticide.

Thus, the present invention provides compositions capable of undergoing adhesion promoting, crosslinking reactions to form polymeric networks with controlled release characteristics.

DETAILED DESCRIPTION OF THE INVENTION

In our co-pending application Ser. No. 927,721, filed July 24, 1978, now U.S. Pat. No. 4,172,904 it was disclosed that a mixture consisting of a hydrolyzable organic titanium compound or a partial hydrolyzate thereof, a hydrolyzable silane or an organopolysiloxane containing hydrolyzable silane groups or partial hydrolyzates thereof, an organopolysiloxane containing hydroxyl groups or functional groups which are hydrolyzable to hydroxyl groups and an insecticide, are capable of undergoing crosslinking reactions to form adherent polymeric networks for the controlled release of the insecticide incorporated therein. It has now been found that the organic titanium compounds and the hydrolyzable silanes and organopolysiloxanes containing hydrolyzable silane groups of the co-pending application may also be used with the carbinol-containing polymers of the present invention.

The hydrolyzable titanium compounds which are suitable for use in the practice of the present invention are the tetraesters, tetraanhydrides and tetraamides of orthotitanic acid.

The titanium tetraesters have the formula:

$$Ti(OR)_4$$

where R is an aliphatic hydrocarbon radical of less than about 20 carbon atoms and may be saturated or unsaturated and acyclic or cyclic. Thus, R may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. Titanium orthoesters where R is the same or mixed are suitable for use in the present invention. Partially hydrolyzed orthoesters may also be used if the hydrolysis has not rendered them insoluble in organic solvents and they still retain alkoxy groups.

The titanium tetraanhydrides have the formula:

$$Ti(OCOR')_4$$

where R′ is an aliphatic hydrocarbon radical of less than about 20 carbon atoms and may be saturated or unsaturated and acyclic or cyclic. Thus, R′ may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. The anhydrides or acylates may also be prepared from aliphatic acids which contain more than one carboxyl group, such as maleic acid, fumaric acid, etc. Titanium acylates where R′ is the same or mixed are suitable for use in the present invention. Mixed alkoxytitanium acylates are also useful. These are prepared by the reaction of a a tetraester with an acid or anhydride or of a tetraanhydride with an alcohol under anhydrous conditions. Partially hydrolyzed acylates may also be used.

The titanium tetraamides have the formula:

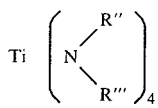

where R″ is hydrogen, alkyl or aryl and R‴ is alkyl or aryl. The alkyl groups may be saturated or unsaturated and acyclic or cyclic and include methyl, ethyl, propyl, butyl, amyl, octyl, stearyl, oleyl, etc. groups.

The titanium polymers prepared by partial hydrolysis of the monomeric titanium orthoesters, acylates and amides, per se or in admixture, as well as by partial hydrolysis of mixed orthoesters, acylates and amides may also be used in the practice of the present invention.

While hydrolyzability is a general characteristic of the tetraesters, tetraanhydrides and tetraamides of orthotitanic acid which may be used in the practice of the present invention, the rate of hydrolysis is a function of the nature of the hydrocarbon substituent. Thus, the presence of methyl, ethyl and other lower alkyl substituents results in rapid hydrolysis while higher alkyl substituents result in slower hydrolysis. In the latter case it is possible to use water as a diluent or dispersing medium during the preparation and handling of the active compositions, and as the hydrolyzing reactant as the composition is applied or after it is applied to the substrate.

An alternative approach to delayed hydrolysis is the use of an organic titanium chelate. The chelates which are suitable for use in the practice of the present invention are either water soluble or solvent soluble and hydrolyze slowly in aqueous systems per se or when the pH is changed or the temperature is raised.

The titanium chelates are derivatives of bi- or multifunctional compounds in which one of the functional groups is usually hydroxyl or enolic carbonyl and the other group is hydroxyl, carboxyl, carbonyl or amino. Thus, the titanium chelates are derivatives of glycols, hydroxy acids, dicarboxylic acids, diketones, ketoesters or alkanolamines. Representative chelates include chelates of 2-methylpentane-2,4-diol, 2-ethylhexane-1,3-diol, 2-methylpentane-1,3-diol, 2-propylheptane-1,3-diol, lactic acid, glycolic acid, citric acid, tartaric acid, hydroxystearic acid, oxalic acid, acetylacetone, ethyl acetoacetate, diethanolamine, triethanolamine and the like.

The titanium chelates are generally prepared by the reaction of a titanium alkoxide such as tetraisopropyl titanate and the appropriate bi- or multifunctional compound. The preparation and properties of the titanium chelates are disclosed in Kirk-Othmer Encyclopedia of Chemical Technology, John Wiley & Sons, New York, 2nd Edition, Volume 20, pages 464–468 (1969). The preparation of aqueous solutions of the titanium chelates is described in "Tyzor Organic Titanates", E.I. duPont de Nemours & Co., Organic Chemicals Department, Technical Bulletin D-5258. The disclosures of each of the hereinabove identified references are incorporated herein by reference.

The hydrolyzable silanes suitable for use in the practice of the present invention have the formula:

$$R_n SiX_{4-n}$$

where R is a monovalent hydrocarbon radical, X is a hydrolyzable group such as halogen, alkoxy, acyloxy, hydrogen and the like, and n is an integer from 0 to 2, inclusive. When X is an alkoxy group OR′, or an acyloxy group OCOR′, R′ may be methyl, ethyl, propyl, isopropyl, butyl, isobutyl, secondary butyl, 2-ethylhexyl or other aliphatic hydrocarbon radical of less than 10 carbon atoms. Preferably R′ is a lower alkyl radical of no more than 4 carbon atoms. All of the X's may be the same or they may be different. The hydrocarbon radical R may be cyclic or acyclic, saturated or unsaturated, aliphatic or aromatic and include the alkyl, aryl, alkenyl, aralkenyl, cycloalkyl, cycloalkyl and heterocyclic radicals such as methyl, ethyl, propyl, isopropyl, butyl, isobutyl, secondary butyl, tertiary butyl, amyl, hexyl, vinyl, allyl, chloroallyl, methallyl, crotyl, butadienyl, phenyl, dichlorophenyl, pentachlorophenyl, xylyl, benzyl, styryl, cinnamyl, furfuryl, cyclohexyl, cyclopentadienyl, cyclopentenyl, pyridyl, etc. radicals. The hydrocarbon R may also be a substituted alkyl R″(CH$_2$)$_x$ where x is an integer from 1 to 20 inclusive and R″ is a polar and/or reactive functionality such as acryloxy, methacryloxy, glycidoxy, epoxycyclohexyl, mercapto, amino, ureido, halo, etc. radicals. There are numerous commercial materials of this type which are commonly known as organofunctional silane coupling agents or adhesion promoters.

The monomeric hydrolyzable silanes may be subjected to partial hydrolysis to promote the formation of condensation products which are still hydrolyzable silanes and are suitable for use in the practice of the present invention.

The organopolysiloxanes containing pendant or terminal hydrolyzable silane radicals, suitable for use in the practice of the present invention, have the formula:

$$P-(SiX_n)_m$$

where P is an organopolysiloxane as hereinafter defined, X is a hydrolyzable group such as halogen, alkoxy, acyloxy, hydrogen, and the like, n is an integer from 2 to 3 and m is an integer from 1 to 20. When X is an alkoxy group OR′ or an acyloxy group OCOR′, R′ may be methyl, ethyl, propyl, isopropyl, butyl, isobutyl, secondary butyl, 2-ethylhexyl or other aliphatic hydrocarbon radical of less than 10 carbon atoms. Preferably, R′ is a lower alkyl radical of no more than 4 carbon atoms. All the X's may be the same or they may be different.

The organopolysiloxanes are well known in the art and contain the structural unit:

where R and R′ are oxygen or non-hydrolyzable hydrocarbon or substituted hydrocarbon radicals and are the same or different. When R and R′ are hydrocarbon radicals, they may be acyclic or cyclic, saturated or unsaturated and include aliphatic radicals such as methyl, ethyl, vinyl, propyl, allyl, butyl, crotyl, hexyl, decyl, dodecyl, hexadecyl, octadecyl, octadecenyl radicals and the like as well as halogenated or other substituted aliphatic radicals, aromatic radicals such as phenyl, biphenyl, phenoxyphenyl and naphthyl radicals as well as halogenated and other substituted aromatic radicals, aralkyl radicals such as benzyl and phenylethyl radicals, alkylaryl radicals such as tolyl and xylyl radicals, cycloaliphatic radicals such as cyclopropyl, cyclopentyl, cyclopentenyl, cyclohexyl and cyclohexenyl radicals and heterocyclic radicals such as furfuryl radicals.

The organopolysiloxanes may be linear, branched or both linear and branched. The polysiloxane may be predominantly a monoorganopolysiloxane, a diorganopolysiloxane, a copolymer containing monoorganosiloxane units and diorganosiloxane units, a copolymer containing triorganosiloxane units and SiO$_2$ units and the like. Notwithstanding the predominant structure, the organopolysiloxane may contain varying amounts of other structural units, in addition to hydrolyzable silane radicals.

The polysiloxanes containing hydrolyzable silane radicals, suitable for use in the practice of the present invention, may be prepared from organopolysiloxanes which are well known in the art. The latter may be prepared by various procedures including controlled hydrolysis of appropriate precursors as well as ring opening polymerization of cyclic organopolysiloxanes.

The controlled hydrolysis and cohydrolysis of RSiX$_3$, R$_2$SiX$_2$, R$_3$SiX and SiX$_4$, where X is a hydrolyzable radical as previously defined, yields organopolysiloxanes containing monoorganosiloxane, diorganosiloxane, triorganosiloxane and SiO$_2$ units, respectively. The relative proportions of said units in the organopolysiloxane are determined by employing the appropriate proportions of hydrolyzable precursors. In order to be useful in the preparation of polysiloxanes containing hydrolyzable silane radicals, the precursor organopolysiloxanes must be readily soluble or dispersible in organic solvents and contain residual reactive radicals such as hydroxyl, alkoxyl, acyloxyl, halogen, hydrogen, vinyl, allyl and the like.

The polymerization of cyclic organopolysiloxanes provides another route to the preparation of organopolysiloxanes containing reactive radicals which may be employed in the preparation of the organopolysiloxanes containing hydrolyzable silane radicals which are suitable for use in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization or in that they contain hydrolyzable groups which upon further hydrolysis may proceed to a more advanced stage of polymerization, if they have not been rendered insoluble in organic solvents, are suitable precursors for the preparation of the organopolysiloxanes containing hydrolyzable silanes which may be used in the practice of the present invention.

The organopolysiloxanes containing hydrolyzable silanes may be prepared by reactions well known in the art. Thus, reaction of an organopolysiloxane containing hydroxyl groups with excess silicon tetraacetate yields the triacetoxysilane.

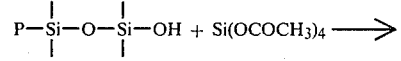

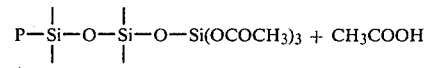

Similarly, reaction with an alkyl or aryltriacetoxysilane yields the corresponding diacetoxysilane, as disclosed in U.S. 3,035,016, the disclosure of which is incorporated herein by reference.

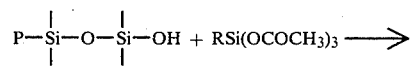

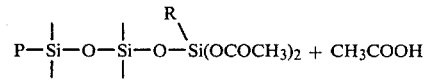

The reaction of an organopolysiloxane containing SiH units, e.g., as prepared by hydrolysis and cohydrolysis of a dichlorosilane with an unsaturated trialkoxysilane or triacyloxysilane in the presence of chloroplatinic acid, yields an organopolysiloxane containing hydrolyzable radicals, suitable for use in the practice of the present invention.

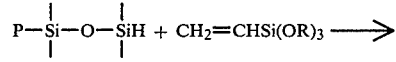

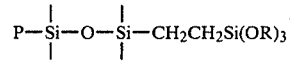

Organopolysiloxanes containing vinyl unsaturation, e.g., as prepared by cohydrolysis of mixtures of various chlorosilanes including vinylalkylchlorosilanes, may be reacted with trialkoxysilane to yield organopolysiloxanes containing hydrolyzable silane radicals suitable for use in the present invention.

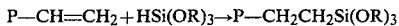

Alternative methods of preparing organopolysiloxanes suitable for use in the practice of the present invention will be obvious to those skilled in the art. Notwithstanding the method of preparation, the presence of SiX$_{2-3}$ radicals as pendant or terminal units in an organopolysiloxane renders it suitable for use in the present invention.

The organopolysiloxanes containing hydrolyzable silane radicals may be fluids of low or high viscosity or even solids. The physical appearance of the polysiloxane is dependent upon the nature of the R and R' radicals, the presence of linear or branched structures as well as the molecular weight. Notwithstanding the physical appearance of the polysiloxane, the important requirement for utility in the practice of the present invention is the presence of hydrolyzable silane radicals. Mixtures of such polysiloxanes are suitable for use in the present invention.

While hydrolyzability is a general characteristic of the silanes which may be used in the practice of the present invention, the rate of hydrolysis is a function of the nature of the hydrocarbon substituent in the hydrolyzable group. Thus, the presence of methyl radicals results in rapid hydrolysis while higher alkyl radicals result in slower hydrolysis. In the latter case, it is possible to use water as a diluent or dispersing medium during the preparation and handling of the active compositions, and as the hydrolyzing reactant as the composition is applied or after it is applied to the substrate.

The carbinol-containing polymers which are suitable for use in the practice of the present invention, include synthetic polymers, natural polymers and chemically modified natural polymers.

Polyalkylene oxides prepared by reaction of alkylene oxides such as ethylene oxide, propylene oxide, styrene oxide, epichlorohydrin, etc., with compounds containing active hydrogen atoms are reactive components in the compositions of the present invention. The effective polyethers may be obtained by oxyalkylation of polyfunctional active hydrogen compounds containing hydroxyl, phenolic, carboxyl, amino, amido, mercapto and other groups. The functional groups may be terminal or pendant groups on linear or branched simple molecules or polymers and the latter may be random, alternating, block or graft copolymers.

Polyesters containing pendant or terminal hydroxyl groups are capable of undergoing crosslinking reactions with the hydrolyzable compounds of the present invention. Effective polyesters include saturated polyesters based on glycol-dicarboxylic acid or glycol-dicarboxylic acid anhydride condensation. Unsaturated polyesters based on maleic anhydride-glycol condensation and similar polyesters are also crosslinked by the hydrolyzable metal compounds. Alkyd resins, containing pendant unsaturation from tung oil, linseed oil, etc., and having branched structures from the incorporation of glycerol or pentaerythritol into the glycol—acid or —anhydride reaction mixture are also suitable crosslinkable polymers.

Polycaprolactone polyester polyols prepared by the reaction of caprolactone with polyol or similar initiators represent an inherently useful group of saturated polyesters with terminal hydroxyl groups, in that they are biodegradable and provide a route to a crosslinked polymer matrix which may be degraded after completing its function as a controlled release matrix.

Epoxy resins containing internal hydroxyl groups, hydrolyzed epoxy resins containing terminal and penultimate hydroxyl groups, reduced epoxy resins containing terminal or internal hydroxyl groups, hydrolyzed epoxy ester resins, etc. are crosslinkable polymers in the present invention. The epoxy resins may be based on bisphenols, glycols, polyols, novolac phenolic resins, epoxidized polybutadiene or other unsaturated diene or vinyl polymer or copolymer, epoxidized soybean oil, etc. The hydroxyl-containing epoxy resins and hydrolyzed epoxy or epoxidized resins undergo crosslinking with the hydrolyzable metal compounds of the present invention to provide adherent polymer matrices or networks.

Formaldehyde-condensation products with phenols, aromatic amines such as aniline or heterocyclic amines such as melamine, contain methylol groups which are crosslinkable with the hydrolyzable metal compounds. Condensation products of other aldehydes are also effective.

The methylol groups of phenol— and amine—formaldehyde condensates may be partially etherified to increase solubility and to reduce crosslink density of the polymeric network formed on interaction with the hydrolyzable metal compound. The phenolic hydroxyl groups in a phenol-formaldehyde condensate may also be partially etherified.

Copolymers of hydroxyalkyl acrylates and methacrylates with other acrylic, vinyl or diene monomers, have crosslinkable hydroxyl groups whose concentration can be controlled by the monomer concentration. Other hydroxyl-containing copolymerizable monomers may be used, including N-methylolacrylamide, dihydroxypropyl methacrylate, etc. Suitable hydroxyl-containing polymers may also be prepared by post-reaction of suitable copolymers, e.g., methylolation of acrylamide copolymers with formaldehyde or other aldehydes, oxyalkylation of acrylic or methacrylic acid copolymers with alkylene oxide, hydrolysis of glycidyl methacrylate copolymers, reaction of glycidyl methacrylate copolymers with alkanolamines, etc.

In addition to the copolymerization of hydroxyl-containing monomers including allyl alcohol, alloxyethanol, 5-norbornene-2-methanol and the like, a route to hydroxyl-containing polymers includes the use of hydroxyl-containing catalysts or catalysts convertible to hydroxyl groups. Thus, hydroxyl-containing polybutadiene and other diene polymers and copolymers may be prepared by radical copolymerization or homopolymerization using hydrogen peroxide or $\beta$-hydroxyethyl alkyl peroxides as radical catalyst. Anionic polymerization of a diene monomer with lithium metal, followed by reaction of the resultant polymer with ethylene oxide yields a polydiene with terminal hydroxyl groups.

The hydrolysis of poly(allyl acetate), poly(vinyl acetate) and copolymers of allyl acetate or vinyl acetate or other allyl or vinyl esters yields polymers with hydroxyl groups. Partial hydrolysis of these homopolymers or copolymers yields copolymers containing hydroxyl groups and residual unhydrolyzed functionality. The hydrolyzed polymers may be reacted with aldehydes such as formaldehyde, butyraldehyde and benzaldehyde to yield formals and acetals containing residual hydroxyl groups capable of undergoing crosslinking. Oxyalkylation of the hydrolyzed polymers yields crosslinkable hydroxyalkyl derivatives.

Cellulose, starch, dextran, chitin and similar polyhydric natural polymers are useful in the practice of the present invention. In order to increase the solubilities of these materials in solvents, where necessary, ether and ester derivatives may be used, e.g., methyl cellulose, hydroxypropyl cellulose, cellulose acetate, cellulose acetate butyrate, etc.

Hydroxyl groups may be appended to polyamides and other polymers containing amide linkages, including block polyester-polyamides or polyether-polyamides, etc., or random copolymers containing amide linkages, including natural polymers such as polypeptides, by treatment with formaldehyde. The resultant methylolated amide functionality is crosslinkable by the hydrolyzable metal compounds of this invention. The polyamides may be of the 6,6-nylon type, prepared by the condensation of a dibasic acid and a diamine, including dimer acids, or of the 6-nylon type, prepared by the ring-opening polymerization of a lactam or the condensation of an aminoalkanoic acid.

Since the hydrolyzable compounds of use in the present invention are polyfunctional, it is generally desirable that the reactive hydroxyl-containing polymer be of low molecular weight and/or have a low hydroxyl content to control crosslink density.

The preferred compositions of the present invention contain hydroxyl-containing polymers and hydrolyzable silanes and titanium compounds in weight ratios wherein the ratio of hydroxyl-containing polymer of the sum of silane and titanium compound is from 0.1/99.9 to 99.9/01 and the ratio of silane to titanium compound is from 0.1/99.9 to 99.9/0.1.

The use of titanates and titanium chelates for the crosslinking of hydroxyl-containing polymers, particularly those used in paint vehicles and printing inks, is well known to those skilled in the art. The use of titanates permits more rapid cure at lower temperatures than could otherwise be obtained.

The toughness, heat resistance, solvent resistance and other properties of coatings based on alkyd resins (M. A. Lerman, Journal of Coatings Technology, 48, 37 (December 1976), polyester resins (U.S. Pat. Nos. 3,074,818 and 3,382,203), bisphenol A-based epoxy resins (U.S. Pat. No. 2,742,448) and other hydroxyl-containing resins are improved on crosslinking with hydrolyzable titanates and titanium chelates.

The drying time and temperature of printing inks containing nitrocellulose (U.S. Pat. No. 2,732,799) and other polyhydroxy compounds are reduced by the use of organic titanates and chelates.

Cellulose (P. Legally and H. Legally, TAPPI, 39, No. 11 (1956) and cellulose acetate fibers (U.S. Pat. No. 3,033,698) are crosslinked in the presence of titanium chelates. The disclosures of each of the hereinabove identified references are incorporated herein by reference.

The organic titanates have been used as catalysts for the polymerization of many types of polysiloxanes. Their use permits more rapid cures at lower temperatures than could otherwise be obtained. In many of these reactions, the titanates serve as catalysts and also crosslink the polysiloxane structure (U.S. Pat. Nos. 2,732,320; 3,014,826; 3,647,846; 3,015,637 and 2,721,855). The disclosures of each of the hereinabove identified references are incorporated herein by reference.

The use of hydrolyzable silanes as adhesion promoting agents is well known. The silane "coupling agents" act as bridges between polymers and fillers or reinforcing agents and permit increased filler loadings, higher reinforcement levels and improved processing and end-product properties in thermosetting resins, thermoplastic resins and elastomers (J. G. Marsden, Plastics Compounding, 1, No. 2, 32 (July/August 1978).

The use of organic titanates and titanium chelates to modify solid surfaces in order to improve adhesion is well known. The titanium compounds are generally applied to the solid surface of a metal, glass or polymer to form an amorphous film of titanium dioxide upon hydrolysis. The hydrolyzed primed surface functions as a polar surface for lamination to a polymeric film or metallic foil or bonding to a coating (U.S. Pat. Nos. 2,751,314; 2,768,909 and 2,838,418).

It is surprising, in view of the disclosures of the prior art, that in the presence of moisture, at ambient temperature, an organic titanate or chelate and a hydrolyzable silane can simultaneously crosslink a hydroxyl-containing polymer and promote adhesion to a solid surface. It is even more surprising that a pesticide can be incorporated in such a reactive system and the resultant composition, upon application to a suitable surface and reaction with moisture at ambient temperature, provide an adherent polymeric network or matrix capable of controlling the release of a pesticide incorporated therein.

Insecticides which may be used in the practice of this invention include any of the compounds well known in the art for use as insecticides such as those set forth in Chemical Week, June 21, 1972, pages 39–64; Chemical Week, July 26, 1972, pages 19–41; and Commercial and Experimental Organic Insecticides (1974 Revision), Entomological Society of America, Special Publication 74-1, October 1974. Some common insecticides which may be used include the following:

| | |
|---|---|
| Pyrethrins | Toxaphene |
| Malathion | Chlordane |
| Parathion | Dursban |
| Methylparathion | Baygon |
| Phorate | DDT |
| Sevin | Diazinon |

The insecticides which may be used in the practice of this invention also include bacterial insecticides such as *Bacillus popilliae* and *Bacillus thuringiensis* and viral insecticides such as the Heliothis virus. These have been described in Chemical & Engineering News, 35, No. 30, 18 (July 28, 1975), the disclosure of which is incorporated herein by reference.

Fungicides which may be used in the practice of this invention include any of the compounds well known in the art for use as fungicides, including those set forth in Chemtech, 7, No. 5, May, 1977, pages 302–305, the disclosure of which is incorporated herein by reference. Some common fungicides which may be used include the following:

| | | |
|---|---|---|
| Anilazine | Carboxin | Karathane |
| 6-Azauracil | Chloroneb | Pyrazophos |
| Benomyl | Dodemorph | Terrazole |
| Binapacryl | Dodine | Thiophanate |
| Blastin | Folpet | Tridemorph |
| Carbofuran | Glyodin | Triforine |
| Captan | Griseofulvin | Dexon |

Herbicides which may be used in the practice of this invention include any of the compounds well known in the art for use as herbicides, including those set forth in Chemtech, 7, No. 6, June, 1977, pages 374–379, the disclosure of which is incorporated herein by reference. Some common herbicides which may be used include the following:

| | |
|---|---|
| Alachor | DSMA |
| Ammonium sulfamate | EPTC |
| Atrazine | Fluometuron |
| Bentazon | Glyphosate |
| Bromacil | Linuron |
| Chloramben | Metribuzin |
| Dalapon | Paraquat |
| 2,4-D | Picloram |
| Diuron | Trifluralin |

The pesticide is included in the composition in an amount sufficient to exert a pesticidal action on the immediate environment surrounding the substrate. The amount of pesticide will be dependent upon several factors such as the composition and thickness of the cured polymeric matrix, the nature of the pesticide, i.e., liquid or solid, the presence of active hydrogen functionality, the duration of pesticidal action desired, etc. The optimum amount of pesticide to be included may readily be determined by those skilled in the art. Generally, from about 1 part by weight of pesticide to 0.5 to 1000 parts of the combined weight of polymer, silane and titanium compound is satisfactory.

The compositions of this invention may include volatile diluents such as aliphatic or aromatic hydrocarbons, e.g., Stoddard Solvent, mineral spirits, V&P naphtha, cyclohexane, petroleum ether, benzene, toluene, xylene, etc., halogenated hydrocarbons such as perchloroethylene and fluorocarbons or volatile fluid polysiloxanes such as dimethylpolysiloxane fluids. The compositions may be prepared by merely admixing the various components. Before admixing, the components may be dispersed or dissolved in a diluent such as previously described. The compositions may also be prepared in aqueous media when slowly hydrolyzing and/or stable components are present.

The compositions of this invention may be applied to a large number of substrates. The substrate should be one which contains active hydrogen atoms which provide sites for coupling with the polymer-silane-titanium compound system, e.g., hydroxyl groups, amino groups, etc. Thus, various plants such as ornamental bushes, trees, flowers, greenhouse plants, lawns, crops (e.g., wheat, corn, soy beans, barley, oats, cotton, jute, sisle), fruits, vegetables, berry bushes, nut trees, olive trees, fig trees, grape vines; various animals such as household pets (e.g., cats, dogs), farm animals such as dairy cattle, beef cattle, horses, sheep, chickens, turkeys, swine, goats, zoo animals, etc. Non-plant and animal uses include spraying surfaces of structures such as buildings and various rooms in buildings, such as kitchens, bathrooms, closets including wood or plaster board walls and floor tile to protect against roaches, termites, flying insects, rug insects, ants, etc. Various containers such as bags and cardboard or wooden boxes may also serve as substrates in accordance with the practice of this invention.

The compositions of this invention may be applied to the substrate by brushing, spraying, dipping or any other known technique for applying a fluid composition to a solid substrate. It may be applied in the form of an aerosol mist or fog, propelled by conventional pressurized volatile halohydrocarbon, hydrocarbon or compressed gas propellants, an air propelled mist blower, a fog generator, or other suitable means.

Although this invention should not be limited thereby, it is believed that upon application of the compositions of this invention to a suitable substrate in an ambient atmosphere, evaporation of the volatile diluent, if any is present, and exposure to atmospheric moisture results in the hydrolysis of both the hydrolyzable titanium compound and the hydrolyzable silane, followed by condensation of the $Ti(OH)_x$ and the $Si(OH)_y$ groups generated thereby with each other and with the hydroxyl groups present on the polymer, to form a cross-linked polymer-polymetalloxane matrix containing entrapped or occluded pesticide. Simultaneously, the $Ti(OH)_x$ and $Si(OH)_y$ groups promote the adhesion of the polymer-polymetalloxane matrix and the pesticide therein to the substrate. Adhesion to the substrate is due at least in part to the fact that the polymer-polymetalloxane matrix is coupled to the substrate by reaction through active hydrogen atoms on the substrate. In this manner, the pesticide is held on the substrate to such an extent that it cannot be physically brushed off, blown off or washed off by rain. Further, as a result of its entrapped condition to rapid evaporation, sublimation or extraction of the pesticide is retarded. However, due to the permeability of the polymer to organic compounds, said evaporation or sublimation is not completely inhibited, resulting in controlled release of the pesticide.

When water is present in the compositions of this invention, said water is generally added shortly before application of the composition to a suitable substrate, and hydrolysis of the titanium compound and the silane may begin before or during application to said substrate. However, hydrolysis continues after said application and is followed by condensation of the TiOH and SiOH groups generated thereby with the hydroxyl groups present on the polymer and the active hydrogen atoms on the substrate.

When a water stable titanium compound, e.g., an organic titanium chelate such as the lactic acid chelate or the triethanolamine chelate, is present, the aqueous composition may be prepared long before application to the substrate. However, an acid or acid-generating compound is added to the aqueous composition containing the triethanolamine chelate or a base or base-generating compound is added to the composition containing the lactic acid chelate, shortly before application to the substrate. The resultant change in the pH promotes hydrolysis of the titanium chelate, which may begin before or during application to the substrate. However, hydrolysis continues after said application and is followed by condensation of the TiOH groups generated thereby with the SiOH groups, the hydroxyl groups on the polymer and the active hydrogen atoms on the substrate.

The rate of release of the pesticide may be controlled by adjusting the extent of crosslinking, e.g., by adjusting the ratio of polymer and hydrolyzable silane and titanium compounds, the thickness of the polymer coating, i.e., by modifying the concentration of reactive components in the solution thereof, or by adding a non-volatile, non-reactive extender for the crosslinked polymer. The latter may have the same structure as the hydroxyl-containing polymer except for the absence of reactive functionality or have a solubility parameter in the same range as that of the polymer. The extender functions essentially as a plasticizer and appropriate plasticizers or extenders for a particular hydroxyl-containing polymer are well known to those skilled in the art.

Typical plasticizers or extenders for hydroxyl-containing polyalkylene oxides, e.g., polyethylene oxide, polyoxyalkylated polyols, polytetrahydrofuran or polytetramethylene glycol, as well as polyesters including polycaprolactone polyols, contain polyether linkages and are free of hydroxyl groups, e.g., dipropylene glycol dibenzoate, polyethylene glycol distearate, and the like. Acrylic copolymers containing hydroxyalkyl acrylates or methacrylates may be extended by simple esters such as dioctyl phthalate or azelates or trimellitates or polymeric esters such as poly(ethylene-copropylene adipate) which has been end-capped by esterification so that it is free of hydroxyl groups or acrylic copolymers such as poly(butyl acrylate) or poly(ethylhexyl acrylate), preferably of low molecular weight. Similar plasticizers or extenders are useful with vinyl acetate homopolymer or copolymers which have been fully or partially hydrolyzed, as well as cellulose ethers or esters, polyvinyl formals or epoxy resins. Sucrose acetate isobutyrate is an effective extender for polyvinyl formal and polyvinyl butyral. Hydrocarbon polymers such as hydroxyl-containing polybutadiene or butadiene copolymers may be extended with polybutadienes, liquid polybutylenes or polypropenes, poly-α-methylstyrenes, terpene resins and other hydrocarbon resins and oils. This partial listing of typical extenders is representative of the low molecular weight compounds and polymers which are compatible with the hydroxyl-containing polymers of interest in the practice of this invention.

In addition to or in lieu of the solvents which function to reduce the viscosity of the compositions of this invention, as well as reduce the thickness of the polymer coating, volatile alcohols such as ethanol, isopropanol, butanol and the like may be included in the composition to prevent premature hydrolysis of the hydrolyzable crosslinking agent with resultant gelation and precipitation.

Other additives which may be incorporated into the compositions of this invention include stabilizers against environmental degradation, such as antioxidants and ultraviolet stabilizers, odor masking compounds and perfumes, dyes, pigments, fillers, etc.

The following examples are illustrative embodiments of the process for utilization of the compositions of this invention. Alternative methods will be obvious to those skilled in the art. Examples I to III illustrate the improved adhesion of the compositions of this invention to a substrate, as compared to the adhesion of a commercial "spreader-sticker" which is used to improve the retention of pesticide deposits under adverse weather conditions. The other examples illustrate the controlled release pesticidal effectiveness of the compositions of this invention. In the tables in the Examples, the numbers refer to the amount of materials in parts by weight.

EXAMPLE I

Solutions of (a) a hydroxyl-terminated polycaprolactone, having an average molecular weight of 540 and an average hydroxyl number of 310, designated as Niax Polyol PCP-0300 by Union Carbide Corp., and (b) a mixture of the polycaprolactone polyol PCP-0300, methyltriethoxysilane, designated as A-162 by Union Carbide Corp., and tetraisopropyl titanate (TPT), were prepared in methyl ethyl ketone (MEK) and applied to glass slides for determination of adhesion.

A few drops of each solution was placed on a weighed glass slide. A glass rod was rolled over the solution to spread the material uniformly over the lower four-fifths of the slide. The coated slide was air dried for 4 hours and then placed in a 50% relative humidity chamber for 18 hours. The slide was then weighed to determine the weight of the coating which ranged from 2 to 5 mg., covering an area of 15 sq. cm. The coated side was inserted into a slit rubber stopper and mounted over the center of a Waring Blender. The coated side faced the moving water which completely covered the coating. The Blender was operated at its highest speed for 5 min. The slide was air dried overnight and then weighed to determine the amount of coating retained on the slide after the treatment in the Blender. The averaged results of duplicate tests are summarized in Table I.

TABLE I

| | Adhesion of Titanate-Silane-Polycaprolactone Polyol Composition | | | | | |
|---|---|---|---|---|---|---|
| | Composition, parts | | | | Solids | Retention |
| No. | PCP-0300 | TPT | A-162 | MEK | % | % |
| 1 | 4 | — | — | 6 | 40 | 0 |
| 2 | 4 | 1 | 1 | 4 | 60 | 79 |

The adhesion of the coating composition, as measured by the retention, is dramatically increased concurrently with the crosslinking of the polyol by the hydrolyzed titanate-silane mixture.

The solution of polycaprolactone polyol, titanate and silane in MEK was mixed with a pyrethroid composition, as follows:

| | Solids, % of total |
|---|---|
| 0.05 g pyrethroids | 3.3 |
| 0.25 g piperonyl butoxide | 16.7 |
| 0.20 g petroleum distillate | |
| 0.80 g PCP-0300 | 53.3 |
| 0.20 g TPT | 13.3 |
| 0.20 A-162 | 13.3 |
| 0.80 g MEK | |

The pyrethroid-containing solution was coated on a glass slide. The coated slide was dried, moisture cured and subjected to treatment with water in the Waring Blender, as described above. The amount of retained coating was 58%, indicating that the adhesion was only slightly decreased by the presence of the pyrethroids.

EXAMPLE II

Solutions of (a) a saturated poly(ethylene-co-propylene adipate) polyester having a hydroxyl number of 51, designated as Fomrez 50 by Witco Chemical Co., and (b) a mixture of the saturated polyester Fomrez 50, tetraisopropyl titanate (TPT) and tetraethyl silicate (TES), were prepared in xylene and applied to glass slides for determination of adhesion. The coated slides were dried, moisture cured for 18 hours and subjected to treatment with water in the Waring Blender, as described in Example I. The results are summarized in Table II.

TABLE II

| | Adhesion of Titanate-Silane-Polyester Composition | | | | | |
|---|---|---|---|---|---|---|
| | Composition, parts | | | | Solids | Retention |
| No. | Fomrez 50 | TPT | TES | Xylene | % | % |
| 3 | 3 | 2 | 1 | 14 | 30 | 52 |
| 4 | 3 | — | — | 7 | 30 | 0 |

The adhesion of the polyester is greatly increased concurrently with its crosslinking by the titanate-silane mixture.

The polyester-titanate-silane solution was mixed with a pyrethroid composition which was then coated on a glass slide. The coated slide was dried, moisture cured and subjected to treatment with water in the Waring Blender, as described earlier. The pyrethroid-containing coating solution had the following composition:

| | Solids, % of total |
|---|---|
| 0.05 g pyrethroids | 5.6 |
| 0.25 g piperonyl butoxide | 27.8 |

-continued

| | Solids, % of total |
|---|---|
| 0.20 g petroleum distillate | |
| 0.30 g Fomrez 50 | 33.3 |
| 0.20 g TPT | 22.2 |
| 0.10 g TES | 11.1 |
| 1.40 g xylene | |

The amount of retained coating after the treatment with water was 61%, indicating that the adhesion was not decreased by the presence of the pyrethroids.

EXAMPLE III

Kalo "Bio-Film", manufactured by Kalo Laboratories, Inc., Petaluma, Calif., is used commercially as a "spreader-sticker for agricultural sprays". According to the technical brochure entitled "Kalo Bio-Film spreader-sticker. Helps your spray form a tough protective film on fruit or leaf", Bio-Film forms a tough, elastic non-drying film on leaf or fruit to protect active spray ingredients, e.g., insecticides, against sun, rain, wind and overhead irrigation water. The "principal functioning agents" in Bio-Film are alkylarylpolyethoxyethanol, free and combined fatty acids, glycol ethers, dialkyl benzenedicarboxylate and isopropanol and the material is added to an aqueous spray solution before application of the latter to crops. Bio-Film is reported to contain 97.7% active ingredients.

In order to compare the adhesion of Kalo Bio-Film with the adhesion of our polymeric compositions, solutions containing 10% Bio-Film and either 90% isopropanol or 90% water, were coated on glass slides, air dried for 24 hours and subjected to treatment with water in the Waring Blender, as described in Example I. The amount of retained coating was 11% and 6%, respectively, as compared with the greater than 50% retention of the compositions of this invention.

EXAMPLE IV

A plasticized hydroxyl-terminated butadiene copolymer-titanate-silane solution containing (a) a liquid 83/17 weight ratio butadiene-acrylonitrile copolymer having a molecular weight of 2300, a 20% 1,2, 65% trans-1,4 and 15% cis-1,4 microstructure, and a hydroxyl content of 0.63 milliequivalents/gram (HT-PBAN), (b) a liquid polybutadiene having a molecular weight of 3400 and a 25% 1,2 40% trans-1,4 and 35% cis-1,4 microstructure, designated as Lithene PH-4 by Lithium Corporation of America, (c) tetraisopropyl titanate (TPT), and (d) tetraethyl silicate (TES), was prepared as a 1% solution in xylene. The components were present in the following weight proportions:

| HT-PBAN | 0.3 |
|---|---|
| TPT | 0.1 |
| TES | 0.2 |
| Lithene PH-4 | 0.6 |
| Xylene | 118.8 |

The butadiene copolymer-titanate-silane solution was mixed with a pyrethroid composition to yield an insecticide-containing solution which was compared with an additive-free pyrethroid composition for insecticidal behavior. The components of the two compositions were as follows:

| | Insecticide Solution | |
|---|---|---|
| | A | B |
| Pyrethroids | 0.1 | 0.1 |
| Piperonyl butoxide | 0.5 | 0.5 |
| Petroleum distillate | 0.4 | 0.4 |
| Isopropanol | — | 99.0 |
| HT-PBAN | 0.247 | — |
| TPT | 0.083 | — |
| TES | 0.165 | — |
| Lithene PH-4 | 0.495 | — |
| Xylene | 98.01 | — |

A disposable plastic syringe was used to place the test solution on a 4×4 inch glass panel. The solution was uniformly spread over the panel with the tip of the syringe. The treated panels were conditioned for 24 hours in a chamber at 78° F. and 42% relative humidity. Ten adult male German cockroaches, *Blatella germanica* (Linnaeus), were exposed to the 1 day residue for 24 hours under a 100×15 mm petri dish. The test was conducted in duplicate. The same treated panels were reexposed to cockroaches after 7 days.

The percent mortality of cockroaches exposed to the treated glass panels is summarized below:

| | Insecticide Solution | |
|---|---|---|
| Residue age | A | B |
| 1 day | 100 | 100 |
| 7 days | 65 | 0 |

The residue from the control insecticide solution B was ineffective and failed to kill any of the exposed cockroaches after 7 days, while the residue from insecticide solution A, containing the butadiene copolymer-titanate-silane composition, killed 65% of the exposed cockroaches after 7 days.

EXAMPLE V

A plasticized polyester-titanate-silane solution containing (a) a saturated poly(ethylene-co-propylene adipate) polyester having a hydroxyl number of 51, designated as Fomrez 50 by Witco Chemical Co., (b) dipropylene glycol dibenzoate (Benzoflex 9–88), (c) tetraisopropyl titanate (TPT), and (d) tetraethyl silicate (TES), was prepared as a 1% solution in xylene. The components were present in the following weight proportions:

| Fomrez 50 polyester | 0.3 |
|---|---|
| TPT | 0.2 |
| TES | 0.1 |
| Benzoflex 9-88 | 0.6 |
| Xylene | 118.8 |

The polyester-titanate-silane solution was mixed with a pyrethroid composition to yield an insecticide-containing solution which was compared with an additive-free pyrethroid composition for insecticidal behavior. The components of the two compositions were as follows:

| | Insecticide Solution | |
|---|---|---|
| | A | B |
| Pyrethroids | 0.1 | 0.1 |
| Piperonyl butoxide | 0.5 | 0.5 |

-continued

| | Insecticide Solution | |
| --- | --- | --- |
| | A | B |
| Petroleum distillate | 0.4 | 0.4 |
| Isopropanol | — | 99.0 |
| Fomrez 50 | 0.247 | — |
| TPT | 0.165 | — |
| TES | 0.083 | — |
| Benzoflex 9-88 | 0.495 | — |
| Xylene | 98.01 | — |

The insecticidal properties of solutions A and B were evaluated using adult cockroaches as the test species and glass as the test surface, as described in Example IV. The treated glass panels were exposed, in duplicate, to cockroaches after 1 and 7 days.

The percent mortality of cockroaches exposed to the treated glass panels is summarized below:

| | Insecticide Solution | |
| --- | --- | --- |
| Residue age | A | B |
| 1 day | 100 | 100 |
| 7 days | 30 | 0 |

The residue from the control insecticide solution B was ineffective and failed to kill any of the exposed cockroaches after 7 days, while the residue from insecticide solution A, containing the saturated polyester-titanate-silane composition, killed 30% of the exposed cockroaches after 7 days.

What is claimed is:

1. A composition capable of undergoing hydrolysis under ambient conditions to form a polymeric network capable of controlling the release of an insecticide consisting essentially of:
   (a) a carbinol-containing organic polymer;
   crosslinking agents for said polymer comprising (b) a hydrolyzable silane selected from the group consisting of (1) a hydrocarbon substituted hydrolyzable silane, (2) an organopolysiloxane containing hydrolyzable silane groups and (3) a partial hydrolyzate of (1) and/or (2), and (c) a hydrolyzable titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines, and
   (d) a pesticide.

2. The composition of claim 1 wherein the hydrocarbon substituted hydrolyzable silane has the formula $R_nSiX_{4-n}$ where R is a monovalent hydrocarbon radical, X is a hydrolyzable group selected from the group consisting of halogen, alkoxy, acyloxy and hydrogen, and n is an integer from 0 to 2.

3. The composition of claim 1 wherein the organopolysiloxane containing hydrolyzable silane groups has the formula $P-(SiX_n)_m$ where P is an organopolysiloxane, X is a hydrolyzable group selected from the group consisting of halogen, alkoxy, acyloxy and hydrogen, n is an integer from 2 to 3, and m is an integer from 1 to 20.

4. The composition of claim 3 wherein the organopolysiloxane contains the structural unit:

wherein R''' and R'''' are oxygen or non-hydrolyzable hydrocarbon or heterocyclic radicals.

5. The composition of claim 4 wherein the non-hydrolyzable radicals are selected from the group consisting of acyclic or cyclic, saturated or unsaturated aliphatic radicals, aromatic radicals, aralkyl radicals and alkylaryl radicals.

6. The composition of claim 1 wherein the weight ratio of a/(b+c) is within the range 0.1/99.9 to 99.9/0.1 and the weight ratio b/c is within the range 0.1/99.9 to 99.9/0.1.

7. A composition capable of undergoing hydrolysis under ambient conditions to form a polymeric network capable of controlling the release of an insecticide, consisting essentially of:
   (a) a carbinol-containing organic polymer;
   crosslinking agents for said polymer comprising (b) a hydrolyzable silane selected from the group consisting of (1) a hydrocarbon substituted hydrolyzable silane, (2) an organopolysiloxane containing hydrolyzable silane groups and (3) a partial hydrolyzate of (1) and/or (2), and (c) a hydrolyzable titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines;
   (d) a non-volatile, non-reactive extender;
   (e) a pesticide, wherein the weight ratio of a/(b+c) is within the range 0.1/99.9 to 99.9/0.1 and the weight ratio b/c is within the range 0.1/99.9 to 99.9/0.1.

8. A composition capable of undergoing hydrolysis under ambient conditions to form a polymeric network capable of controlling the release of an insecticide, consisting essentially of:
   (a) a carbinol-containing organic polymer;
   crosslinking agents for said polymer comprising (b) a hydrolyzable silane selected from the group consisting of (1) a hydrocarbon substituted hydrolyzable silane, (2) an organopolysiloxane containing hydrolyzable silane groups and (3) a partial hydrolyzate of (1) and/or (2), and (c) a hydrolyzable titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines;
   (d) a volatile diluent; and
   (e) a pesticide, wherein the weight ratio of a/(b+c) is within the range 0.1/99.9 to 99.9/0.1 and the weight ratio b/c is within the range 0.1/99.9 to 99.9/0.1.

9. A composition capable of undergoing hydrolysis under ambient conditions to form a polymeric network capable of controlling the release of an insecticide, consisting essentially of:
   (a) a carbinol-containing organic polymer;

crosslinking agents for said polymer comprising (b) a hydrolyzable silane selected from the group consisting of (1) a hydrocarbon substituted hydrolyzable silane, (2) an organopolysiloxane containing hydrolyzable silane groups and (3) a partial hydrolyzate of (1) and/or (2), and (c) a hydrolyzable titanium compound or a partial hydrolyzate thereof, said titanium compound being selected from the group consisting of tetraesters, tetraanhydrides, tetraamides and chelates of glycols, hydroxy acids, dicarboxylic acids, diketones, ketoesters and alkanolamines;

(d) a non-volatile, non-reactive extender;

(e) a volatile diluent; and (f) a pesticide, wherein the weight ratio of a/(b+c) is within the range 0.1/99.9 to 99.9/0.1 and the weight ratio b/c is within the range 0.1/99.9 to 99.9/0.1.

10. A composition as defined in claim 1 wherein said pesticide is an insecticide.

* * * * *